(12) United States Patent
Tanaka et al.

(10) Patent No.: US 11,337,593 B2
(45) Date of Patent: May 24, 2022

(54) ENDOSCOPE APPARATUS AND VIDEO PROCESSOR

(71) Applicant: OLYMPUS CORPORATION, Tokyo (JP)

(72) Inventors: Satoshi Tanaka, Hachioji (JP); Yoichiro Sakanoue, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 605 days.

(21) Appl. No.: 16/130,007

(22) Filed: Sep. 13, 2018

(65) Prior Publication Data

US 2019/0008372 A1    Jan. 10, 2019

Related U.S. Application Data

(63) Continuation of application No. PCT/JP2016/082038, filed on Oct. 28, 2016.

(30) Foreign Application Priority Data

Mar. 17, 2016    (JP) .................................. 2016-054090

(51) Int. Cl.
*A61B 1/04*    (2006.01)
*H04N 7/18*    (2006.01)
(Continued)

(52) U.S. Cl.
CPC .................. *A61B 1/04* (2013.01); *A61B 1/00* (2013.01); *A61B 1/06* (2013.01); *A61B 1/0676* (2013.01);
(Continued)

(58) Field of Classification Search
CPC .... A61B 1/04; A61B 1/00; A61B 1/06; A61B 1/0676; A61B 1/00006; H04N 7/18; G02B 23/24; G02B 23/26; G02B 23/2461
(Continued)

(56) References Cited

U.S. PATENT DOCUMENTS 6,219,091 B1 *   4/2001  Yamanaka .........  G02B 23/2484
                                                600/109
2007/0123751 A1 *  5/2007  Takahashi ..........  A61B 1/00006
                                                600/118
(Continued)

FOREIGN PATENT DOCUMENTS

EP          2856928 A1       4/2015
JP       2007-318581 A      12/2007
(Continued)

OTHER PUBLICATIONS

International Search Report dated Jan. 24, 2017 issued in PCT/JP2016/082038.

*Primary Examiner* — John W Miller
*Assistant Examiner* — Omer Khalid
(74) *Attorney, Agent, or Firm* — Scully, Scott, Murphy & Presser, P.C.

(57) ABSTRACT

An endoscope apparatus includes a light emitting element, an image pickup device of a rolling shutter scheme, and a control section. The control section performs control for switching between a first illumination mode for irradiating light on a subject in a readout period in which readout of an electric signal is performed in order for each of lines in the image pickup device and a second illumination mode for not irradiating light on the subject in the readout period. The control section controls the image pickup device to perform electronic shutter processing in all-line exposure period in which exposure of a plurality of lines is simultaneously performed in a frame corresponding to timing when one of the first illumination mode and the second illumination mode is switched to the other illumination mode.

5 Claims, 5 Drawing Sheets

(51) Int. Cl.
    *A61B 1/06*    (2006.01)
    *A61B 1/00*    (2006.01)
    *G02B 23/24*   (2006.01)
    *G02B 23/26*   (2006.01)

(52) U.S. Cl.
    CPC ......... *G02B 23/24* (2013.01); *G02B 23/2461* (2013.01); *H04N 7/18* (2013.01); *A61B 1/00006* (2013.01); *G02B 23/26* (2013.01)

(58) Field of Classification Search
    USPC .......................................................... 348/68
    See application file for complete search history.

(56)            References Cited

U.S. PATENT DOCUMENTS

2014/0203170 A1* 7/2014 Ono ..................... H04N 5/2354
                                                    250/208.1
2014/0364690 A1* 12/2014 Seto ...................... A61B 1/045
                                                    348/70

FOREIGN PATENT DOCUMENTS

JP          2010-262224 A     11/2010
WO      WO 2013/157368 A1     10/2013
WO      WO 2013/175908 A1     11/2013

* cited by examiner

ENDOSCOPE APPARATUS AND VIDEO PROCESSOR

CROSS REFERENCE TO RELATED APPLICATION

This application is a continuation application of PCT/JP2016/082038 filed on Oct. 28, 2016 and claims benefit of Japanese Application No. 2016-054090 filed in Japan on Mar. 17, 2016, the entire contents of which are incorporated herein by this reference.

BACKGROUND OF INVENTION

1. Field of the Invention

The present invention relates to an endoscope apparatus and a video processor.

2. Description of the Related Art

Conventionally, endoscope apparatuses have been widely used in a medical field and an industrial field. An insertion section of an endoscope apparatus is inserted into a subject. The endoscope apparatus irradiates illumination light on a site to be examined, receives, with an image pickup device, reflected light from the site to be examined, and generates an endoscopic image, which is a subject image.

In recent years, there has been an endoscope apparatus in which a CMOS image sensor is used as an image pickup device. In the CMOS image sensor, a rolling shutter scheme for performing exposure and readout with timing shifted for each of lines is adopted. Processing from the exposure to the readout is performed at different timing for each of the lines.

In the case of the CMOS image sensor, when pulse illumination is performed, exposure unevenness occurs depending on light emission timing of illumination light. Therefore, a technique for correcting the exposure unevenness has been proposed as disclosed in International Publication No. 2013/157368.

In this proposal, exposure unevenness is eliminated to prevent deterioration in image quality by correcting, on the basis of light amounts of illumination lights corresponding to respective horizontal lines at a time when an image (an image having a gentle gradation) is obtained by performing exposure with a CMOS under illumination of a predetermined light-adjusting mode, the image obtained by the exposure to bring the image close to an image (an image without a gradation) at a time when the light amounts of the illumination lights corresponding to the respective horizontal lines are the same.

SUMMARY OF THE INVENTION

An endoscope apparatus according to an aspect of the present invention includes: a light emitting section configured to emit light for illuminating a subject; an image pickup section of a rolling shutter scheme including a plurality of lines each including a plurality of pixels that receive light reflected from the subject illuminated by the light emitted by the light emitting section and generate an electric signal, the image pickup section being configured to read out the electric signal in order for each of the lines, start exposure in order from a line for which readout of the electric signal is completed, and generate an image pickup signal of one frame; an illumination control section configured to perform control for switching between a first pattern for irradiating the light on the subject in a readout period in which the readout of the electric signal is performed in order for each of the lines in the image pickup section and a second pattern for not irradiating the light on the subject in the readout period; and an electronic-shutter control section configured to control the image pickup section to perform electronic shutter processing in an all-line exposure period in which exposure of the plurality of lines is simultaneously performed in a frame corresponding to timing when one pattern of the first pattern and the second pattern is switched to another pattern by the illumination control section.

A video processor according to an aspect of the present invention is a video processor that receives an input of an electric signal from an image pickup section of a rolling shutter scheme and generates an endoscopic image, the image pickup section including a plurality of lines each including a plurality of pixels that receive light reflected from a subject illuminated by light emitted by a light emitting section that emits light for illuminating the subject, and generate the electric signal, the image pickup section being configured to read out the electric signal in order for each of the lines, start exposure in order from a line for which readout of the electric signal is completed, and generate an image pickup signal of one frame, the video processor including: an illumination control section configured to perform control for switching between a first pattern for irradiating the light on the subject in a readout period in which the readout of the electric signal is performed in order for each of the lines in the image pickup section and a second pattern for not irradiating the light on the subject in the readout period; and an electronic-shutter control section configured to control the image pickup section to perform electronic shutter processing in an all-line exposure period in which exposure of the plurality of lines is simultaneously performed in a frame corresponding to timing when one pattern of the first pattern and the second pattern is switched to another pattern by the illumination control section.

DETAILED DESCRIPTION OF THE PREFERRED EMBODIMENT(S)

An embodiment of the present invention is explained below with reference to the drawings.

Figure 1:
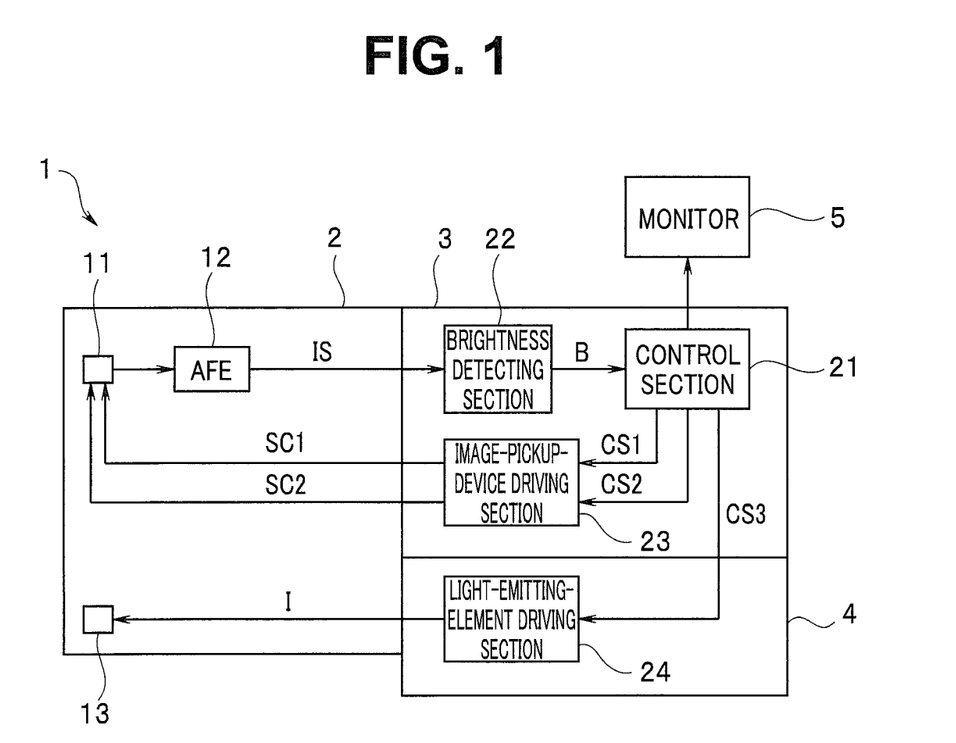
FIG. 1 is a block diagram showing a configuration of an endoscope apparatus according to an embodiment.

FIG. 1 is a block diagram showing a configuration of an endoscope apparatus according to an embodiment. As shown in FIG. 1, an endoscope apparatus 1 of this embodiment includes an endoscope 2, a video processor 3, a light source apparatus 4, and a monitor 5. Note that, in FIG. 1, only components related to control of a rolling shutter of this embodiment are shown. The other components are omitted.

The endoscope 2 includes an image pickup device 11, an analog front-end section (hereinafter referred to as AFE section) 12, and a light emitting element 13.

The image pickup device 11 functioning as an image pickup section is a CMOS image sensor. The image pickup device 11 is driven by an image-pickup-device driving section 23 explained below to output an image pickup signal to the AFE section 12. The image pickup device 11 receives light reflected from a subject illuminated by light emitted by the light emitting element 13 and generates an electric signal. The image pickup device 11 includes a light receiving section including a plurality of horizontal lines, each of which includes a plurality of pixels. The image pickup device 11 is an image pickup device of a rolling shutter scheme configured to read out the electric signal in order for each of the lines and start exposure in order from a line for which the readout of the electric signal is completed and generate an image pickup signal of one frame. The image pickup device 11 has a function of an electronic shutter. The image pickup device 11 is driven by an image-pickup-device driving section 23 explained below. The image pickup device 11 can reset electric charges at predetermined timing.

The AFE section 12 performs noise reduction processing, amplification processing, and the like on an inputted image pickup signal, which is an analog signal, and then converts the image pickup signal into a digital signal and outputs the image pickup signal to the video processor 3.

The light emitting element 13 is a light emitting diode (LED) configured to emit, for example, white light. The light emitting element 13 is a light emitting section driven by a light-emitting-element driving section 24 explained below to emit illumination light for illuminating the subject. The image pickup device 11 and the light emitting element 13 are disposed at a distal end portion of an insertion section of the endoscope 2.

The video processor 3 includes a control section 21, a brightness detecting section 22, and an image-pickup-device driving section 23.

The control section 21 includes a central processing unit (CPU), a ROM, and a RAM and performs control of the entire endoscope apparatus 1 and control of the respective sections. More specifically, the control section 21 performs driving control of the image pickup device 11 and the light emitting element 13, generation of an image displayed on the monitor 5 by applying various kinds of image processing to an image pickup signal outputted from the image pickup device 11, recording of the image in a not-shown memory, and the like.

The brightness detecting section 22 is a circuit configured to calculate, on the basis of the image pickup signal IS outputted from the image pickup device 11 of the endoscope 2, brightness of an image from pixel values of a plurality of pixels included in a predetermined range, for example, a frame image entire range.

The image-pickup-device driving section 23 is a circuit configured to generate an image pickup device driving signal SC1 on the basis of an image pickup device control signal CS1 outputted from the control section 21 and drive the image pickup device 11. The image-pickup-device driving section 23 is a circuit configured to generate an electronic shutter driving signal SC2 on the basis of an electronic shutter control signal CS2 outputted from the control section 21 and perform electronic shutter processing of the image pickup device 11. The image pickup device driving signal SC1 includes a synchronization signal for giving exposure timing and readout timing to the image pickup device 11.

The light source apparatus 4 includes a light-emitting-element driving section 24. As explained below, the control section 21 outputs a light emitting element driving control signal CS3 at predetermined timing.

The light-emitting-element driving section 24 is a circuit configured to generate a driving signal I, which is a current signal, on the basis of the light emitting element driving control signal CS3 outputted from the control section 21 and drive the light emitting element 13. Intensity of light emitted by the light emitting element 13 changes according to magnitude, that is, a current value of the driving signal I outputted from the light-emitting-element driving section 24.

The control section 21 controls switching between two illumination modes explained below and controls, in the respective illumination modes, on the basis of a brightness signal B detected by the brightness detecting section 22, intensity of the illumination light emitted by the light emitting element 13 to set brightness of an image to appropriate brightness.

The illumination light emitted from the light emitting element 13 provided at the distal end portion of the insertion section of the endoscope 2 illuminates an observation site of the subject. The image pickup device 11 receives reflected light of the illumination light and generates an image pickup signal IS.

The monitor 5 is a display apparatus such as a liquid crystal display configured to display an endoscopic image and a menu image.

As explained above, the brightness detecting section 22 detects brightness of an image of each of frames on the basis of the image pickup signal IS outputted from the AFE section 12 and outputs the brightness signal B indicating brightness of respective frame images to the control section 21. The control section 21 generates a display image on the basis of the received image pickup signal IS and outputs the light emitting element driving control signal CS3 to the light-emitting-element driving section 24 on the basis of the received brightness signal B.

Therefore, the control section 21 controls the image-pickup-device driving section 23 to drive the image pickup device 11, generates an endoscopic image from image data generated by the rolling shutter scheme, and outputs the endoscopic image to the monitor 5 and displays the endoscopic image.

Control in reducing a light emission amount of the illumination light emitted by the light emitting element 13 from a maximum to a minimum is explained.

Figure 2:
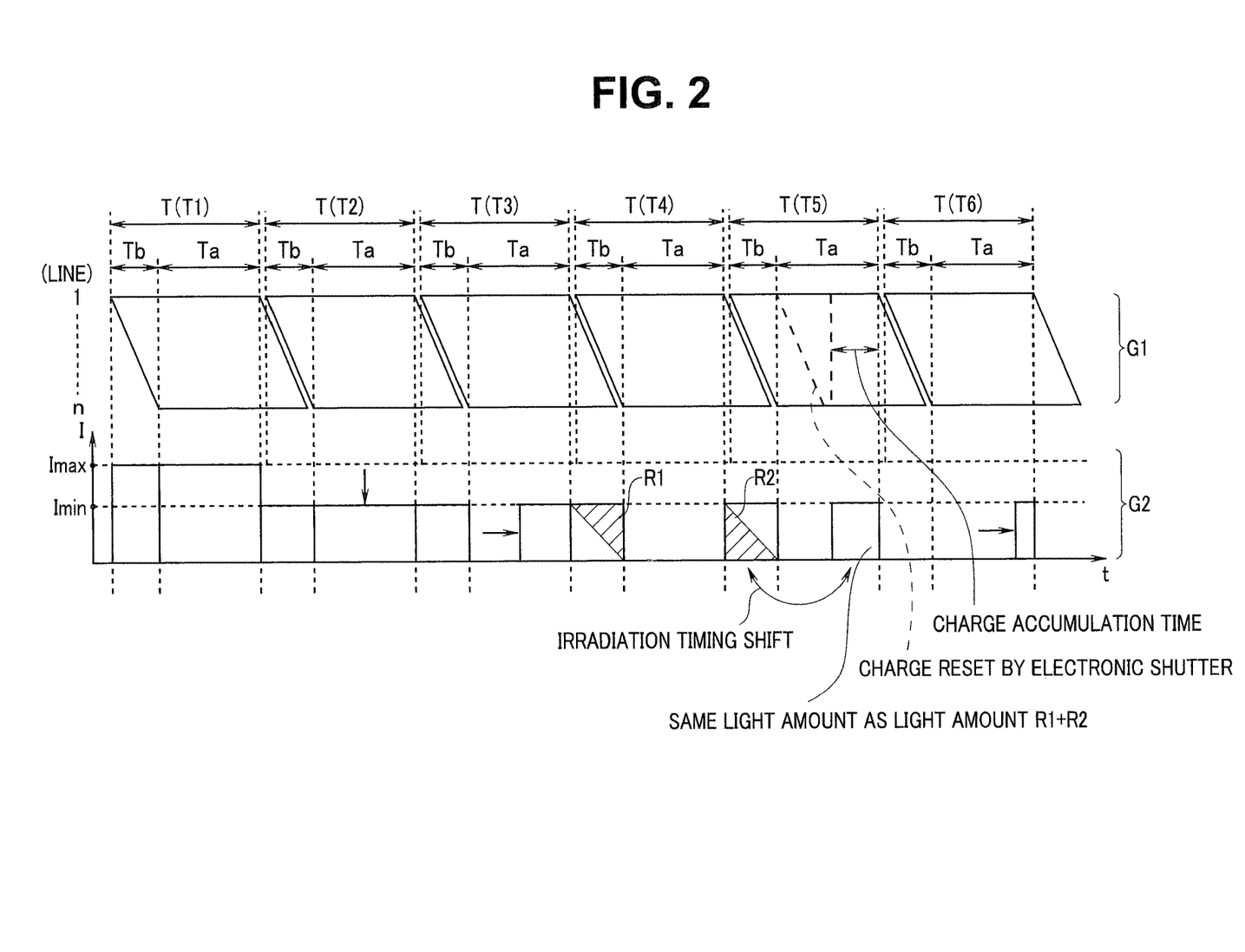
FIG. 2 is a schematic diagram for explaining a relation between an exposure period and a readout period of an image pickup device 11 during image pickup of an endoscope apparatus 1 and an output (a light emission amount: reduced from a maximum to a minimum) of illumination light emitted by a light emitting element 13.

FIG. 2 is a schematic diagram for explaining a relation between an exposure period and a readout period of the image pickup device 11 during image pickup of the endoscope apparatus 1 and an output (a light emission amount: reduced from a maximum to a minimum) of the illumination light emitted by the light emitting element 13.

In FIG. 2, timings of exposure periods and readout periods of respective lines of the image pickup device 11 are schematically shown in a range indicated by G1 in an upper side. A change of the driving signal I flowing in the light emitting element 13 is shown in G2 in a lower side. A horizontal axis is an axis of time t.

The image pickup device 11 is a CMOS image sensor. The image pickup device 11 includes a light receiving section including lines in n rows, each of which includes a plurality of pixels. The image pickup device 11 generates image data by the rolling shutter scheme for performing exposure and readout with timing shifted for each of the lines.

When continuously performing image pickup of a plurality of frames, the image pickup device 11 performs readout of accumulated electric charges for each one horizontal line. A first line (a line in a first row in FIG. 2) of the light receiving section of the image pickup device 11 to an n-th line (n is a natural number; a line in an n-th row in FIG. 2), which is a last line, are sequentially set as a readout line and a pixel signal is read out. Therefore, a time difference occurs in readout timing between the line in the first row and the line in the n-th row.

A period from a start of readout of pixel data in the first line of the image pickup device 11 until an end of readout of pixel data in the n-th line is a video readout period Tb of a CMOS rolling shutter.

A period other than a cyclically generated video readout period Tb, that is, a period in which exposure is simultaneously performed for all the lines is an all-line simultaneous exposure period Ta of the CMOS rolling shutter. As shown in FIG. 2, in a period T of one field or one frame of an image (one cycle of the CMOS rolling shutter) includes the video readout period Tb and the all-line simultaneous exposure period Ta.

Because the rolling shutter scheme is adopted in the image pickup device 11, the video readout period Tb and the all-line simultaneous exposure period Ta alternate. Note that the period T of one field (or one frame), the video readout period Tb, and the all-line simultaneous exposure period Ta are determined by specifications of the image pickup device 11.

As explained above, the image pickup device 11 provided in the insertion section of the endoscope 2 is the image pickup device of the rolling shutter scheme including the plurality of lines that receive reflected light from the subject on which light is irradiated and configured to alternate the video readout period Tb for reading out image pickup signals of the respective lines in order from the plurality of lines and the all-line simultaneous exposure period Ta for simultaneously performing exposure of the plurality of lines.

The driving signal I outputted by the light-emitting-element driving section 24 changes between a predetermined minimum value Imin and a predetermined maximum value Imax. The control section 21 outputs the light emitting element driving control signal CS3 to the light-emitting-element driving section 24. That is, the light emitting element driving control signal CS3 is a signal for setting the driving signal I outputted by the light-emitting-element driving section 24 between the predetermined minimum value Imin and the predetermined maximum value Imax.

When the insertion section of the endoscope 2 is inserted into the subject and an image of an inside of the subject is picked up by the image pickup device 11, the control section 21 outputs, to the light-emitting-element driving section 24, the light emitting element driving control signal CS3 for controlling, according to brightness of the image detected by the brightness detecting section 22, the light emitting element 13 to emit the illumination light at intensity for setting the image to proper brightness. That is, the control section 21 adjusts magnitude of the driving signal I flowing to the light emitting element 13 to thereby execute current level control for performing light adjustment. The current level control is, for example, PAM (pulse amplitude modulation) control.

In FIG. 2, magnitude of a current value of the driving signal I flowing in the light emitting element 13 is smaller in a period T2 than in a period T1. For example, because a distal end of the insertion section approaches the subject, the brightness signal B increases and the intensity of the illumination light needs to be reduced. Therefore, in the period T2, the current value of the driving signal I for driving the light emitting element 13 decreases. In an example shown in FIG. 2, the driving signal I in the period T1 has the maximum value Imax and the driving signal I in the period T2 has the minimum value Imin.

In respective periods of the periods T1 and T2, illumination control is performed in a first illumination mode M1 for emitting illumination light having constant intensity corresponding to brightness of an image in the video readout period Tb and the all-line simultaneous exposure period Ta. That is, the control section 21 usually executes the illumination control by the first illumination mode M1 for emitting illumination light having the same intensity in the all-line simultaneous exposure period Ta and the video readout period Tb in order to obtain an image having appropriate brightness. As explained above, in the first illumination mode M1, the driving signal I is adjusted between the predetermined minimum value Imin and the predetermined maximum value Imax. However, if the distal end portion of the insertion section of the endoscope 2 excessively approaches the subject, brightness of an image is equal to or higher than predetermined brightness even if the driving signal I has the minimum value Imin.

Therefore, in a period T3, in order to reduce the intensity of the illumination light, PWM control for emitting the illumination light in the video readout period Tb and, in the all-line simultaneous exposure period Ta, controlling an illumination light amount according to a time period in which the illumination light is emitted is performed. In a period T4, the time in which the illumination light is emitted is further reduced in the all-line simultaneous exposure period Ta, the illumination light is emitted only in the video readout period Tb, and the illumination light is not emitted in the all-line simultaneous exposure period Ta.

When the illumination light amount is further reduced, from a period T4 to a period T5, a shift of irradiation timing for shifting timing of irradiation from the video readout period Tb to the all-line simultaneous exposure period Ta is performed. At this time, it is desirable to perform the PWM control to set a light amount in the all-line simultaneous exposure period Ta of the period T5 to the same light amount as a light amount R1+R2.

That is, when the intensity of the illumination light is too high if the illumination light is emitted in the all-line simultaneous exposure period Ta and the video readout period Tb because, for example, the distal end of the insertion section is close to the subject, the control section 21 switches the illumination mode to execute the illumination control by a second illumination mode M2 for emitting the illumination light only in the all-line simultaneous exposure period Ta in order to obtain an image having appropriate brightness. In this way, the control section 21 configures an illumination control section configured to perform control for switching between the first illumination mode (a first pattern) M1 for irradiating light on the subject in the video readout period Tb and the second illumination mode (a second pattern) M2 for not irradiating light on the subject in the video readout period Tb.

The second illumination mode M2 is a mode executed when a necessary light amount is small because the illumination light is emitted only in the all-line simultaneous exposure period Ta and the illumination light is not emitted in the video readout period Tb. In the second illumination mode M2, both of current control for increasing or reducing the magnitude of the driving signal I and controlling intensity of light and the PWM control for controlling the illumination light amount according to a time period in which the light is emitted are used. That is, although not shown in the figure, in the second illumination mode M2 as well, the driving signal I is adjusted between the predetermined minimum value Imin and the predetermined maximum value Imax.

The illumination mode switches between the first illumination mode M1 and the second illumination mode M2 according to brightness L of a screen. FIG. 2 shows that, at a time of a shift from the period T4 to the period T5, a shift of the illumination control from the first illumination mode M1 to the second illumination mode M2 is performed.

In this way, the shift of the irradiation timing is performed from the period T4 to the period T5. However, because the illumination light is irradiated in the video readout period Tb of the period T5 as well, an exposure amount decreases from the line 1 to the line n and exposure unevenness occurs.

Therefore, when the illumination mode is switched from the first illumination mode M1 to the second illumination mode M2, the control section 21 outputs the electronic shutter control signal CS2 to the image-pickup-device driving section 23 to control the image-pickup-device driving section 23 to perform the electronic shutter processing in the all-line simultaneous exposure period Ta of the period T5. The image-pickup-device driving section 23 outputs the electronic shutter driving signal SC2 to the image pickup device 11 on the basis of the electronic shutter control signal CS2. Consequently, the image-pickup-device driving section 23 performs the electronic shutter processing in the all-line simultaneous exposure period Ta of the period T5 and resets electric charges accumulated in the video readout period Tb. As a result, a charge accumulation time in the period T5 is set the same in all the lines. Luminance unevenness in the period T5 can be prevented.

In a period T6, a time period in which light is emitted in the all-line simultaneous exposure period Ta is set shorter than the time period in the period T5. That is, duty width of PWM is reduced to a minimum value and the light emission amount of the illumination light is minimized.

Control in increasing the light emission amount of the illumination light emitted by the light emitting element 13 from a minimum to a maximum is explained.

Figure 3:
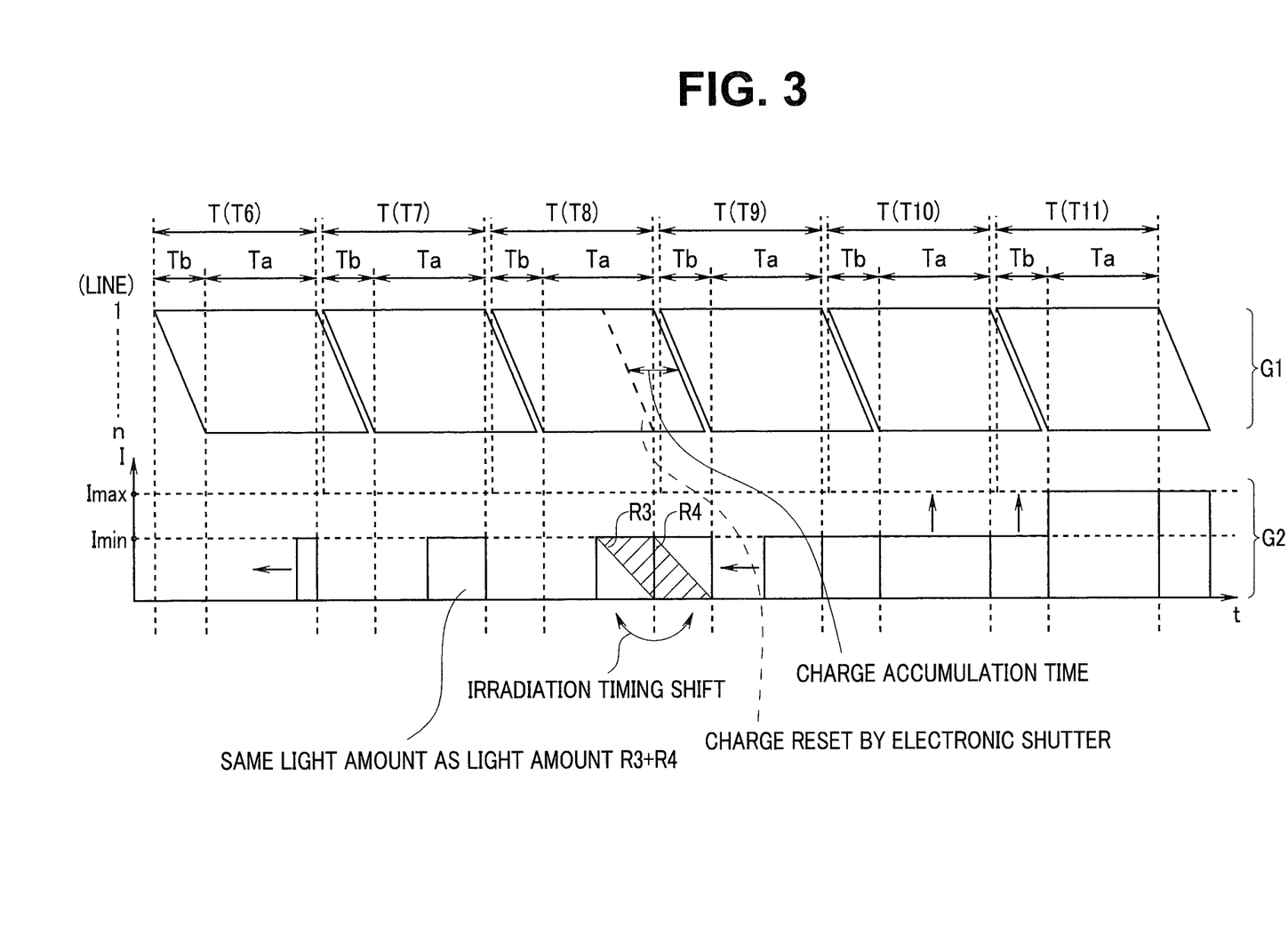
FIG. 3 is a schematic diagram for explaining a relation between the exposure period and the readout period of the image pickup device 11 during the image pickup of the endoscope apparatus 1 and an output (a light emission amount: increased from a minimum to a maximum) of the illumination light emitted by the light emitting element 13.

FIG. 3 is a schematic diagram for explaining a relation between the exposure period and the readout period of the image pickup device 11 during the image pickup of the endoscope apparatus 1 and an output (a light emission amount: increased from a minimum to a maximum) of the illumination light emitted by the light emitting element 13. Note that, in FIG. 3, the same components as the components shown in FIG. 2 is denoted by the same reference numerals and explanation of the component is omitted.

The period T6 is the same as the period T6 shown in FIG. 2. The duty width of the PWM in the all-line simultaneous exposure period Ta is reduced to the minimum value and the light emission amount of the illumination light is minimized. For example, the brightness signal B decreases because the distal end of the insertion section moves away from the subject. The intensity of the illumination light needs to be increased. Therefore, in a period T7, an application time of the driving signal I in the all-line simultaneous exposure period Ta is longer than the application time in the period T6.

When the illumination light amount is further increased, from a period T8 to a period T9, a shift of irradiation timing for shifting timing of irradiation from the all-line simultaneous exposure period Ta to the video readout period Tb is performed. At this time, it is desirable that a light amount in the all-line simultaneous exposure period Ta of the period T7 is the same light amount as a light amount R3+R4.

In this way, the shift of the irradiation timing is performed from the period T8 to the period T9. However, because the illumination light is irradiated in the all-line simultaneous exposure period Ta of the period T8 as well, an exposure amount increases from the line 1 to the line n and exposure unevenness occurs.

Therefore, when the illumination mode is switched from the second illumination mode to the first illumination mode, the control section 21 outputs the electronic shutter control signal CS2 to the image-pickup-device driving section 23 to control the image-pickup-device driving section 23 to perform the electronic shutter processing in the all-line simultaneous exposure period Ta of the period T8. The image-pickup-device driving section 23 outputs the electronic shutter driving signal SC2 to the image pickup device 11 on the basis of the electronic shutter control signal CS2. Consequently, the image-pickup-device driving section 23 performs the electronic shutter processing in the all-line simultaneous exposure period Ta of the period T8 and resets electric charges exposed in the all-line simultaneous exposure period Ta. As a result, a charge accumulation time in the period T8 is set the same in all the lines. Luminance unevenness in the period T8 can be prevented.

As explained above, the control section 21 configures an electronic-shutter control section configured to control the image pickup device 11 to perform electronic shutter processing in the all-line exposure period Ta in a frame corresponding to timing when the illumination mode is switched from the first illumination mode M1 to the second illumination mode M2 or from the second illumination mode M2 to the first illumination mode M1.

When the illumination light amount is further increased, as in periods T10 and T11, the control section 21 adjusts the magnitude of the driving signal I flowing to the light emitting element 13 between the predetermined minimum value Imin and the predetermined maximum value Imax to thereby execute current level control for performing light adjustment.

Operation of the endoscope apparatus 1 is explained.

As explained above, the illumination mode is switches between the first illumination mode M1 and the second illumination mode M2 according to the brightness L of the screen. Processing of switching between the first illumination mode M1 and the second illumination mode M2 is explained.

Figure 4:
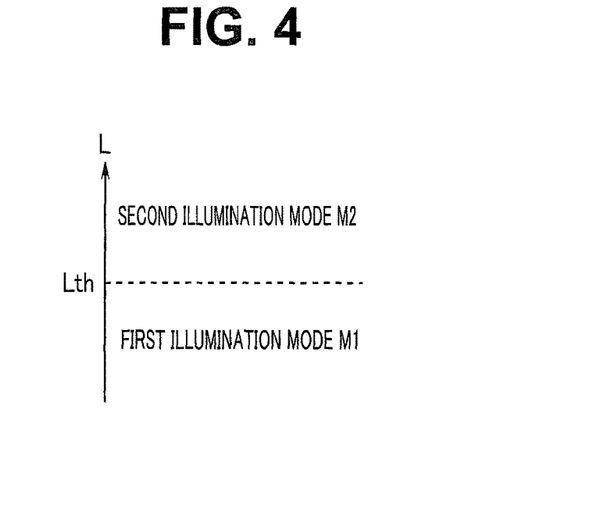
FIG. 4 is a diagram for explaining illumination modes.

FIG. 4 is a diagram for explaining the illumination modes. A vertical axis of FIG. 4 indicates the brightness L. The control section 21 usually controls, on the basis of the brightness signal B detected by the brightness detecting section 22, the intensity of the illumination light emitted by the light emitting element 13 to set brightness of an image to appropriate brightness. However, when the distal end portion of the endoscope 2 is too close to a site to be examined, even if the driving signal I reaches the minimum value Imin, the brightness L of an obtained image is not the appropriate brightness and is equal to or larger than a predetermined threshold Lth.

Therefore, if the brightness L of the image calculated on the basis of the brightness signal B outputted from the brightness detecting section 22 is equal to or larger than the predetermined threshold Lth, the control section 21 executes the illumination control in the second illumination mode M2. If the brightness L of the image is smaller than the predetermined threshold Lth, the control section 21 executes the illumination control in the first illumination mode M1. The switching of the illumination mode is performed when the brightness L is equal to or larger than the predetermined threshold Lth and when the brightness L is smaller than the predetermined threshold Lth.

Figure 5:
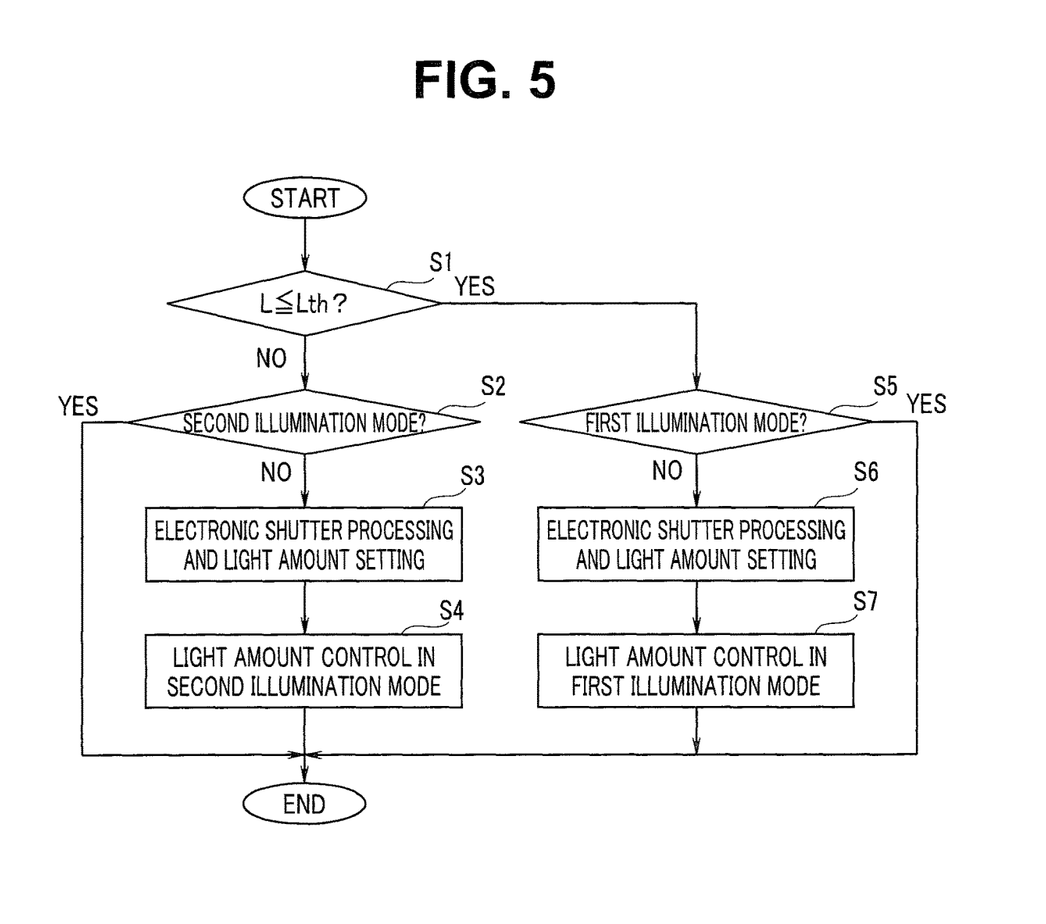
FIG. 5 is a flowchart showing an example of a flow of switching processing of the illumination modes.

FIG. 5 is a flowchart showing an example of a flow of switching processing of the illumination mode. The processing shown in FIG. 5 is always executed when the illumination control is executed in the first illumination mode M1 and the second illumination mode M2.

The control section 21 determines on the basis of the brightness signal B outputted from the brightness detecting section 22 whether the brightness L of the image is equal to or smaller than the predetermined threshold Lth (S1). When the brightness L of the image exceeds the predetermined threshold Lth (NO in S1), the control section 21 determines whether a present illumination mode is the second illumination mode M2 (S2). When the present illumination mode is the second illumination mode M2 (YES in S2), the control section 21 performs no processing.

On the other hand, when the present illumination mode is not the second illumination mode M2 (NO in S2), the control section 21 determines that the illumination mode is switched from the first illumination mode M1 to the second illumination mode M2, preforms the electronic shutter processing and light amount setting (S3), performs light amount control in the second illumination mode M2 (S4), and ends the processing.

In the electronic shutter processing in S3, as shown in FIG. 2, the control section 21 performs the electronic shutter processing in a period before irradiation of the illumination light is started (i.e., a period before the driving signal I is applied) in the all-line simultaneous exposure period Ta of a frame after the illumination mode is switched.

When the brightness L of the image is equal to or smaller than the predetermined threshold Lth (YES in S1), the control section 21 determines whether a present illumination mode is the first illumination mode M1 (S5). When the present illumination mode is the first illumination mode M1 (YES in S5), the control section 21 performs no processing.

On the other hand, when the present illumination mode is not the first illumination mode M1 (NO in S5), the control section 21 determines that the illumination mode is switched from the second illumination mode M2 to the first illumination mode M1, performs the electronic shutter processing and the light amount setting (S6), performs the light amount control in the first illumination mode M1 (S7), and ends the processing.

In the electronic shutter processing in S6, as shown in FIG. 3, the control section 21 performs the electronic shutter processing in a period in which the illumination light is irradiated (i.e., a period in which the driving signal I is applied) in the all-line simultaneous exposure period Ta of a frame at a time when the illumination mode is switched.

As explained above, when switching the illumination mode (when performing the shift of the irradiation timing), the endoscope apparatus 1 resets, with the electronic shutter processing, electric charges accumulated in the video readout period Tb or the all-line simultaneous exposure period Ta to obtain an image having a uniform charge accumulation time in all the lines, that is, uniform brightness in all the lines. As a result, the endoscope apparatus 1 can obtain an image with luminance unevenness reduced without performing high-speed and complicated processing such as gain processing for multiplying a different gain value for each of different lines.

Therefore, with the endoscope apparatus of this embodiment, it is possible to reduce luminance unevenness without performing high-speed and complicated processing.

(Modification)

A modification of the embodiment explained above is explained.

In the embodiment explained above, the electronic shutter processing is performed when the shift of the irradiation timing is performed. However, besides the shift of the irradiation timing, for example, the electronic shutter processing may be performed when a light source is turned OFF.

Figure 6:
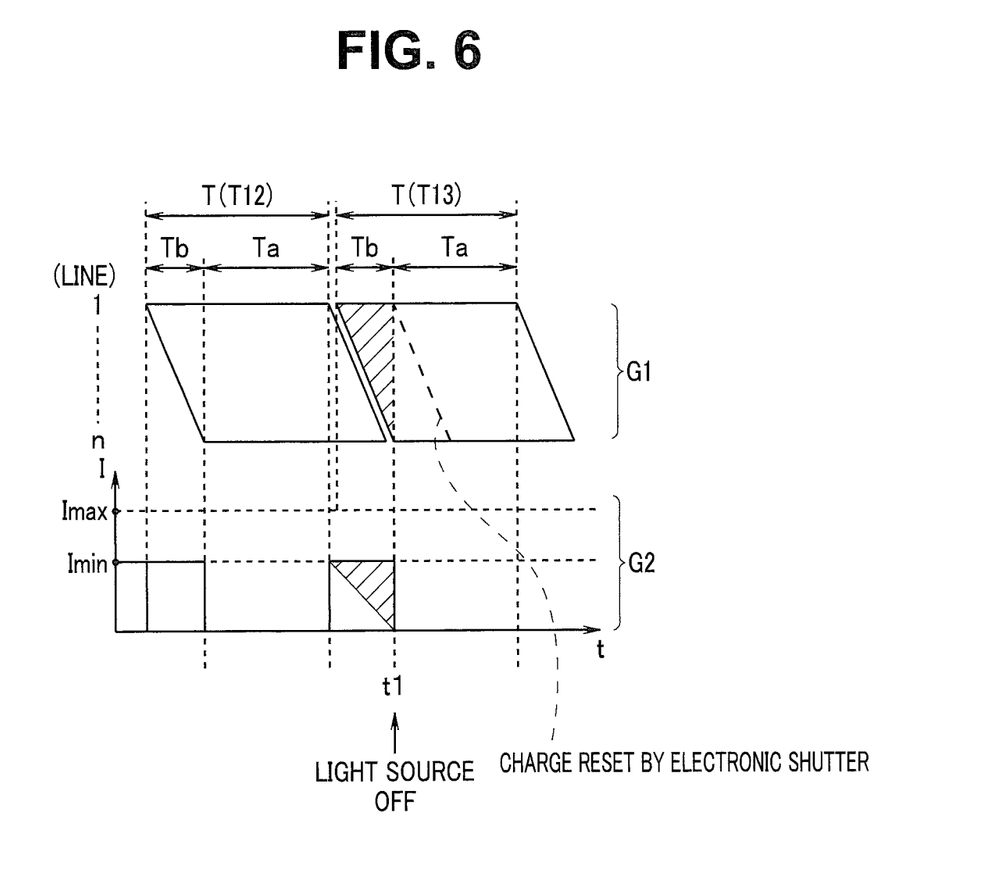
FIG. 6 is a schematic diagram for explaining electronic shutter processing performed when a light source is turned off.

FIG. 6 is a schematic diagram for explaining the electronic shutter processing performed when the light source is turned OFF.

As shown in FIG. 6, when the light source is turned off at time t1, electric charges are accumulated in the video readout period Tb of a period T13. Therefore, the exposure amount decreases from the line 1 to the line n. An image with luminance unevenness is displayed on the monitor 5.

When the light source is turned off, the control section 21 outputs the electronic shutter control signal CS2 to the image-pickup-device driving section 23 to control the image-pickup-device driving section 23 to perform the electronic shutter processing after the light source is turned off. The image-pickup-device driving section 23 outputs the electronic shutter driving signal SC2 to the image pickup device 11 on the basis of the electronic shutter control signal CS2. Consequently, as shown in FIG. 6, the electronic shutter processing is performed after the light source is turned off. The electric charges accumulated in the video readout period Tb of the period T13 are reset. An image without the illumination light irradiated on all the lines is generated.

As a result, with the endoscope apparatus of the modification, for example, in the same manner as when the light source is turned off, as in the embodiment explained above, it is possible to reduce luminance unevenness without performing high-speed and complicated processing besides the shift of the irradiation timing.

Note that the respective steps in the flowchart in this specification may be simultaneously executed with execution order changed or the respective steps may be executed in a different order in every execution unless contrary to characteristics of the steps.

The present invention is not limited to the embodiment and the modification explained above. Various changes, alterations, and the like are possible in a range in which the gist of the present invention is not changed.

What is claimed is:

1. An endoscope apparatus comprising:
   a light source configured to emit light for illuminating a subject;
   an image sensor of a rolling shutter scheme including a plurality of lines each including a plurality of pixels that receive light reflected from the subject illuminated by the light emitted by the light source and generate an electric signal, the image sensor being configured to read out the electric signal in order for each of the lines, start exposure in order from a line for which readout of the electric signal is completed, and generate an image pickup signal of one frame; and a controller comprising hardware, the controller being configured to:

control the light source to switch between a first pattern for irradiating the light on the subject in a readout period in which the readout of the electric signal is performed in order for each of the lines in the image sensor and a second pattern for not irradiating the light on the subject in the readout period;

control the image sensor to perform electronic shutter processing so as to reset electric charges of the line for which the readout of the electric signal is completed in the readout period, and control the image sensor to perform the electronic shutter processing in an all-line exposure period in which exposure of the plurality of lines is simultaneously performed, the electronic shutter processing being performed before the light source emits light, in a frame corresponding to timing when one of the first pattern and the second pattern is switched to an other of the first pattern and the second pattern, the electronic shutter processing being performed such that electric charges, which are accumulated in the frame, are reset in the all-line exposure period.

2. The endoscope apparatus according to claim 1, wherein the second pattern is a pattern for not irradiating the light on the subject in the readout period and irradiating the light in the all-line exposure period, and the controller performs the electronic shutter processing of a rolling shutter scheme in a period before irradiation of the light is started in the all-line exposure period of a frame corresponding to timing when the first pattern is switched to the second pattern.

3. The endoscope apparatus according to claim 1, wherein the first pattern is a pattern for irradiating the light in the readout period and the all-line exposure period, and the controller performs the electronic shutter processing of a rolling shutter scheme in a period in which irradiation of the light is performed in the all-line exposure period of a frame corresponding to timing when the second pattern is switched to the first pattern.

4. The endoscope apparatus according to claim 1, wherein the controller controls the image sensor not to perform the electronic shutter processing in the all-line exposure period of a frame after a frame in which the electronic shutter processing is performed.

5. A video processor that receives an input of an electric signal from an image sensor of a rolling shutter scheme and generates an endoscopic image, the image sensor including a plurality of lines each including a plurality of pixels that receive light reflected from a subject illuminated by light emitted by a light source that emits light for illuminating the subject, and generates an electric signal, the image sensor being configured to read out the electric signal in order for each of the lines, start exposure in order from a line for which readout of the electric signal is completed, and generate an image pickup signal of one frame, the video processor comprising a controller comprising hardware, the controller being configured to:

control the light source to switch between a first pattern for irradiating the light on the subject in a readout period in which the readout of the electric signal is performed in order for each of the lines in the image sensor and a second pattern for not irradiating the light on the subject in the readout period;

control the image sensor to perform electronic shutter processing so as to reset electric charges of the line for which the readout of the electric signal is completed in the readout period, and control the image sensor to perform the electronic shutter processing in an all-line exposure period in which exposure of the plurality of lines is simultaneously performed, the electronic shutter processing being performed before the light source emits light, in a frame corresponding to timing when one pattern of the first pattern and the second pattern is switched to an other of the first pattern and the second pattern, the electronic shutter processing being performed such that electric charges, which are accumulated in the frame, are reset in the all-line exposure period.

* * * * *